(12) United States Patent
Down

(10) Patent No.: US 8,007,830 B2
(45) Date of Patent: Aug. 30, 2011

(54) GRANULE FORMATION

(75) Inventor: Brian Down, Pierrefonds (CA)

(73) Assignee: Merck Frosst Canada & Co., Quebec (CA)

( * ) Notice: Subject to any disclaimer, the term of this patent is extended or adjusted under 35 U.S.C. 154(b) by 0 days.

(21) Appl. No.: 12/069,124

(22) Filed: Feb. 7, 2008

(65) Prior Publication Data

US 2008/0131516 A1 Jun. 5, 2008

Related U.S. Application Data

(63) Continuation of application No. 10/279,595, filed on Oct. 24, 2002, now abandoned.

(60) Provisional application No. 60/339,549, filed on Oct. 26, 2001.

(51) Int. Cl.
*A61K 9/16* (2006.01)
*A01N 43/42* (2006.01)

(52) U.S. Cl. .................................. 424/490; 514/311

(58) Field of Classification Search .............. 424/490; 514/311
See application file for complete search history.

(56) References Cited

U.S. PATENT DOCUMENTS

| | | | |
|---|---|---|---|
| 4,177,254 A | 12/1979 | Khan et al. |
| 5,064,829 A | 11/1991 | Izuhara et al. |
| 5,489,439 A | 2/1996 | Bola |
| 5,565,473 A | 10/1996 | Belley et al. |
| 5,855,914 A | 1/1999 | Koyama et al. |
| 5,869,098 A | 2/1999 | Misra et al. |
| 6,103,735 A | 8/2000 | Aslanian et al. |
| 6,224,907 B1 | 5/2001 | Davar et al. |
| 6,262,077 B1 | 7/2001 | Shih |
| 6,316,029 B1 | 11/2001 | Jain et al. |
| 2003/0031720 A1 | 2/2003 | Laich et al. |

FOREIGN PATENT DOCUMENTS

| | | |
|---|---|---|
| JP | 2258719 | 10/1990 |
| JP | 5092918 | 4/1993 |
| JP | 9067247 | 3/1997 |
| WO | WO 97/16173 | 5/1997 |
| WO | WO 99/32125 A1 | 7/1999 |
| WO | WO 00/30647 A1 | 6/2000 |
| WO | WO 01/37808 A1 | 5/2001 |
| WO | WO 01/51036 A1 | 7/2001 |

OTHER PUBLICATIONS

EP Patent 1441701 EPO Opposition proceeding, Dec. 18, 2008, pp. 1-17.
English Abstract of JP 2258719, 1990.
English Abstract of JP 5092918, 1993.
English Abstract of JP 9067247, 1997.
EP Patent EP1441701 Opposition—Information about result of Opposition Proceedings Jun. 10, 2010, 1 page.
EP Patent 1441701 Opposition—Letter from Opponent with Literature Jul. 1, 2010, 15 pages.
EP Patent 1441701 Opposition—Summons for Oral Proceeding and Preliminary Opinion Mar. 5, 2010, 9 pages.
EP Patent 1441701 Opposition—Letter from Patent Proprietor Feb. 23, 2010, 5 pages.
EP Patent 1441701 Opposition—Reply of Patent Proprietor to Notice of Opposition Jun. 26, 2009, 10 pages.
Minutes of the oral proceedings before the OPPOSITION DIVISIONS, EP-B-1441701, Appl. No. 02 801 836.4, pp. 12, Oct. 6, 2010.
Decision revoking the European Patent, EP-B-1441701, Appl. No. 02 801 836.4, pp. 13, Nov. 26, 2010.

*Primary Examiner* — Robert A Wax
*Assistant Examiner* — Aradhana Sasan
(74) *Attorney, Agent, or Firm* — Mollie M. Yang; Yong Zhao; Valerie J. Camara

(57) ABSTRACT

The present invention relates to oral granules of montelukast sodium.

5 Claims, No Drawings

GRANULE FORMATION

CROSS REFERENCE TO RELATED APPLICATIONS

This application is a Continuation Application of U.S. Ser. No. 10/279,595, filed Oct. 24, 2002 now abandoned, which is based on and claims priority from U.S. Provisional Application Ser. No. 60/339,549, filed Oct. 26, 2001, which is hereby incorporated by reference in its entirety.

BACKGROUND OF THE INVENTION

Montelukast sodium (SINGULAIR®) is a leukotriene receptor antagonist approved for the treatment of asthma in adults and pediatric patients from 2 years old. The drug is currently being studied for the treatment of seasonal allergic rhinitis, as well as for potential use in children as young as 6 months old. Montelukast sodium is currently available as 10 mg film-coated tablets for adults and 4 mg and 5 mg chewable tablets for children.

SUMMARY OF THE INVENTION

The present invention relates to a novel formulation of montelukast sodium in the form of granular powder which may be ingested directly or mixed with food or other comestibles. The novel formulation is suitable for use by patients who either have difficulty swallowing or chewing tablets or who prefer not to do so.

DETAILED DESCRIPTION OF THE INVENTION

The present invention provides a flowable and dispersible pharmaceutical composition which comprises granules having a substrate coated with montelukast sodium, and a lubricant. The granules of the present composition may be prepared by coating the substrate, optionally first agglomerated with a pharmaceutically acceptable binder, with an aqueous solution of montelukast sodium. The resulting drug granules are dried, and blended with a pharmaceutically acceptable lubricant to produce a flowable and dispersible composition suitable for packaging.

In the present invention, the substrate may be any that is pharmaceutically acceptable; typically a sugar such as mannitol, sucrose, lactose, xylitol or the like is used. The substrate is preferably used in a form that is free-flowing, a characteristic that facilitates accurate dosing of the final product granules into unit-dose pouches for market distribution. If the substrate is not free-flowing, it is necessary to agglomerate individual particles into larger granules.

In one embodiment of the granules, the substrate is spray-dried mannitol, which may be prepared by spray-drying an aqueous solution of mannitol using conventional processes. Commercially available spray-dried mannitol (e.g. PEARLITOL® SD 200, Roquette Freres, France) may also be used in the present invention. Individual particles of spray-dried mannitol such as PEARLITOL® SD 200 are generally spherical which imparts to this material its free-flowing property. Mannitol is preferably used because of its sweet, cooling taste and non-hygroscopic nature. The substrate typically comprises from about 95 to about 98% weight of the composition.

In cases where the substrate is very free-flowing on its own it may be used in producing the drug granules without further agglomeration; or optionally, the substrate may be first agglomerated with a pharmaceutically acceptable binder. Suitable pharmaceutically acceptable binders are for example hydroxypropyl cellulose, hydroxypropyl methylcellulose, methylcellulose, ethylcellulose and poly-vinylpyrrolidone. The agglomeration of the substrate particles is carried out by applying an aqueous solution of the binder onto the substrate, for example by spraying a solution of the binder onto a fluidized bed of the substrate. The binder, when used, typically comprises from about 2 to about 5% of the composition. The resultant agglomerated substrate particles are dried and used in the next step.

The substrate particles are coated with montelukast sodium by, for example, spraying an aqueous drug solution directly on to a fluidized bed of the substrate to produce the drug granules. The granulation process results in drug coated granules, which after drying are sized to provide granules of less than about 850 microns. The sized granules are blended with a lubricant and used to fill the final product container.

Montelukast sodium is a known compound and its preparation is disclosed in, for example, U.S. Pat. Nos. 5,565,473 and 5,614,632. For use in the present invention a solution of montelukast sodium in water is used in the granulation process. Montelukast typically comprises from about 0.4% to about 5% of the composition such that each unit dose package would contain the desired amount of montelukast sodium, ranging from about 2 mg to about 20 mg per dose.

One of skill in the art will appreciate that other inert ingredients may be added to the composition to impart to the final product desired properties such as taste or appearance; for example, sweeteners such as aspartame, flavoring compounds, and food colorings may be added.

The dried and sized drug granules are tumble blended with a lubricant to facilitate product flow during unit dosage form filling operation, and to prevent binding of moving metal components during such operation. Suitable lubricants are pharmaceutically acceptable and include, without limitation, magnesium stearate, talc, and the like. The lubricant typically comprises from about 0.25 to about 1% of the composition.

The lubricated granules are used to fill the final unit dosage package, which must provide light and moisture protection for the drug granules. One example of suitable packaging is foil (for example aluminum) pouch or sachet. The foil may be laminated with an outer polyester film that acts as a child-resistant (biting and tearing) barrier. An inner linear low-density polyethylene laminate acts as the heat seal component for the pouches.

Montelukast sodium is a leukotriene receptor antagonist and as such may be used for the treatment and prevention of leukotriene-mediated diseases and disorders. Leukotriene antagonists are useful in the treatment of asthma, allergic rhinitis (including seasonal and perennial), atopic dermatitis, chronic urticaria, sinusitis, nasal polyps, chronic obstructive pulmonary disease, conjunctivitis including rhinoconjunctivitis, migraine, cystic fibrosis, and wheezing secondary to viral (such as respiratory syncytial virus) bronchiolitis, among others.

For the treatment of asthma, the present composition may be administered to patients by either direct placement in the mouth of the patient, or by pre-mixing with a soft food such as applesauce and the like. The established dose of montelukast for asthma is typically about 10 mg per day for an adult, and for children from about 2 to about 5 mg per day. The magnitude of the dose may, however, vary with the nature and the severity of the condition to be treated, and the age, weight and response of the individual patient; a physician of ordinary skill in the art will be able to adjust the typical dose upward or downward to devise a suitable dose and dosing schedule based on the individual characteristics and need of the patient.

For the treatment of allergic rhinitis (including seasonal and perennial), the present composition may be administered to patients by either direct placement in the mouth of the patient, or by pre-mixing with food such as applesauce and the like. The dose of montelukast for allergic rhinitis is about 10 mg per day for an adult, and for children from about 2 to about 5 mg per day. The magnitude of the dose may, however, vary with the nature and the severity of the condition to be treated, and the age, weight and response of the individual patient; a physician of ordinary skill in the art will be able to adjust the typical dose upward or downward to devise a suitable dose and dosing schedule based on the individual characteristics and need of the patient.

For the treatment of atopic dermatitis, the present composition may be administered to patients by either direct placement in the mouth of the patient, or by pre-mixing with food such as applesauce and the like. The dose of montelukast for atopic dermatitis may be about 10 mg per day for an adult, and for children from about 2 to about 5 mg per day. The magnitude of the dose may, however, vary with the nature and the severity of the condition to be treated, and the age, weight and response of the individual patient; a physician of ordinary skill in the art will be able to adjust the typical dose upward or downward to devise a suitable dose and dosing schedule based on the individual characteristics and need of the patient.

For the treatment of chronic urticaria, the present composition may be administered to patients by either direct placement in the mouth of the patient, or by pre-mixing with food such as applesauce and the like. The dose of montelukast for chronic urticaria may be about 10 mg per day for an adult, and for children from about 2 to about 5 mg per day. The magnitude of the dose may, however, vary with the nature and the severity of the condition to be treated, and the age, weight and response of the individual patient; a physician of ordinary skill in the art will be able to adjust the typical dose upward or downward to devise a suitable dose and dosing schedule based on the individual characteristics and need of the patient.

For the treatment of sinusitis, the present composition may be administered to patients by either direct placement in the mouth of the patient, or by pre-mixing with soft food such as applesauce and the like. The dose of montelukast for sinusitis may be about 10 mg per day for an adult, and for children from about 2 to about 5 mg per day. The magnitude of the dose may, however, vary with the nature and the severity of the condition to be treated, and the age, weight and response of the individual patient; a physician of ordinary skill in the art will be able to adjust the typical dose upward or downward to devise a suitable dose and dosing schedule based on the individual characteristics and need of the patient.

For the treatment of nasal polyps, the present composition may be administered to patients by either direct placement in the mouth of the patient, or by pre-mixing with food such as applesauce and the like. The dose of montelukast for nasal polyps may be about 10 mg per day for an adult, and for children from about 2 to about 5 mg per day. The magnitude of the dose may, however, vary with the nature and the severity of the condition to be treated, and the age, weight and response of the individual patient; a physician of ordinary skill in the art will be able to adjust the typical dose upward or downward to devise a suitable dose and dosing schedule based on the individual characteristics and need of the patient.

For the treatment of chronic obstructive pulmonary disease (COPD), the present composition may be administered to patients by either direct placement in the mouth of the patient, or by pre-mixing with soft food such as applesauce and the like. The dose of montelukast for COPD may be about 10 mg per day for an adult, and for children from about 2 to about 5 mg per day. The magnitude of the dose may, however, vary with the nature and the severity of the condition to be treated, and the age, weight and response of the individual patient; a physician of ordinary skill in the art will be able to adjust the typical dose upward or downward to devise a suitable dose and dosing schedule based on the individual characteristics and need of the patient.

For the treatment of conjunctivitis (including rhinoconjunctivitis), the present composition may be administered to patients by either direct placement in the mouth of the patient, or by pre-mixing with food such as applesauce and the like. The dose of montelukast for conjunctivitis may be about 10 mg per day for an adult, and for children from about 2 to about 5 mg per day. The magnitude of the dose may, however, vary with the nature and the severity of the condition to be treated, and the age, weight and response of the individual patient; a physician of ordinary skill in the art will be able to adjust the typical dose upward or downward to devise a suitable dose and dosing schedule based on the individual characteristics and need of the patient.

For the treatment of cystic fibrosis, the present composition may be administered to patients by either direct placement in the mouth of the patient, or by pre-mixing with food such as applesauce and the like. The dose of montelukast for cystic fibrosis may be about 10 mg per day for an adult, and for children from about 2 to about 5 mg per day. The magnitude of the dose may, however, vary with the nature and the severity of the condition to be treated, and the age, weight and response of the individual patient; a physician of ordinary skill in the art will be able to adjust the typical dose upward or downward to devise a suitable dose and dosing schedule based on the individual characteristics and need of the patient.

For the treatment of wheezy kid syndrome, or wheezing secondary to viral (such as respiratory syncytial virus) bronchiolitis, the present composition may be administered to patients by either direct placement in the mouth of the patient, or by pre-mixing with food such as applesauce and the like. The dose of montelukast for chronic urticaria may be about 10 mg per day for an adult, and for children from about 2 to about 5 mg per day. The magnitude of the dose may, however, vary with the nature and the severity of the condition to be treated, and the age, weight and response of the individual patient; a physician of ordinary skill in the art will be able to adjust the typical dose upward or downward to devise a suitable dose and dosing schedule based on the individual characteristics and need of the patient.

The following description of the preparation of the present pharmaceutical composition is by way of example only, and not to be construed as limiting the scope of the invention in any manner.

For the preparation of the drug granules, typically the substrate is charged into a fluid-bed granulator equipped with a top-spray nozzle. An aqueous solution of the binder is sprayed onto the fluidized substrate at a specified rate to form granules. The granules are dried and the dried granules are sprayed with an aqueous solution of montelukast sodium. The result drug granules are dried, and the dried granules are sized to <850 microns and then blended with a lubricant by tumble blending. The lubricated granules are re-blended prior to filling into pouches.

EXAMPLE 1

Preparation of Montelukast Sodium Oral Granules

Granulation of Mannitol. Place into a suitably sized stainless steel container equipped with a high shear agitator: purified water USP (102 kg); while agitating at approximately 300 rpm add hydroxypropyl cellulose LF (HPC, 4.16 kg). Continue mixing at 300 rpm until hydroxypropyl cellulose is completely dissolved by visual inspection. Allow solution to defoam completely prior to use; use the binder solution within 72 hours of manufacture.

Transfer into a fluid bed granulator with a 670 L granulating bowl mannitol (Pearlitol SD 200, Roquette Freres, 194 kg), and spray onto the mannitol in the column the previously made HPC Solution (106 kg) using the following processing parameters:

| | |
|---|---|
| Inlet Air Volume | approx. 2500 scfm |
| Inlet Air Temperature | approx. 68 deg C. |
| Inlet Air Dewpoint | approx. 12 deg C. |
| Atomization Air Flow | approx. 46 scfm |
| Spray Rate | approx. 1310 g/min |

After solution delivery is complete, dry the product in the column to an endpoint of </=0.5% LOD (loss on drying), using the following processing parameters:

| | |
|---|---|
| Inlet Air Volume | approx. 2500 scfm |
| Inlet Air Temperature | approx. 68 deg C. |
| Inlet Air Dewpoint | approx. 12 deg C. |
| Atomization Air Flow | approx. 30 scfm |

Discharge the dried product into unlined stainless steel drums.

Drug Solution Preparation. Place into a suitably sized stainless steel container equipped with a high shear agitator purified water USP (49.0 kg, theoretical amount). While agitating at approximately 230 rpm add montelukast sodium (1.70 kg, theoretical amount). Continue mixing at 230 rpm until montelukast sodium is completely dissolved by visual inspection. Allow solution to defoam completely prior to use (use the drug solution within 24 hours of manufacture). The amount of drug solution prepared reflects a 2% excess of theoretical to account for spray drying. The amount of coating solution required may be adjusted if the coating efficiency of the process changes.

Drug Coating/Drying. Transfer into a fluid bed granulator with a 670 L granulating bowl the dried mannitol granules (198 kg, theoretical amount). Coat the granulation in the column with the montelukast solution (50.7 kg, theoretical amount) using the following processing parameters:

| | |
|---|---|
| Inlet Air Volume | approx. 2500 scfm |
| Inlet Air Temperature | approx. 68 deg C. |
| Inlet Air Dewpoint | approx. 12 deg C. |
| Atomization Air Flow | approx. 35 scfm |
| Spray Rate | approx. 1310 g/min |

After solution delivery is complete, dry the product in the column to an endpoint of </=0.5% LOD, using the following processing parameters:

| | |
|---|---|
| Inlet Air Volume | approx. 2500 scfm |
| Inlet Air Temperature | approx. 68 deg C. |
| Inlet Air Dewpoint | approx. 12 deg C. |
| Atomization Air Flow | approx. 25 scfm |

After drying the dried granules (200 kg, theoretical amount) are sieved through a #20-mesh (approximately 850 micron) screen. Store granulation that passes through the 20 mesh (approximately 850 micron) screen in unlined stainless steel container(s) until lubrication The amount of drug solution listed reflects a 2.14% excess of theoretical to account for spray drying. The amount of coating solution required may be adjusted if the coating efficiency of the process changes. Additionally, the actual amount of drug solution sprayed may be adjusted based on the yield of dried mannitol granulation. The amount of drug solution listed above is the maximum amount that could be sprayed (assuming a 100% yield of mannitol granulation).

Lubrication Add to a 600 L bin the sieved granulation (200 kg, theoretical amount) and Magnesium Stearate (previously screened through a #30-mesh; approximately 600 micron screen, 0.500 kg). Blend the 600 L bin for 10 minutes at approximately 6 rpm. Discharge the lubricated blend into unlined stainless steel drums.

Re-blending Charge to a 600 L bin the lubricated granulation and blend the 600 L bin for 10 minutes at approximately 6 rpm. Store the re-blended granulation in the closed bin until sachet filling.

Sachet Filling Place the 600 L bin with re-blended granulation above the sachet filling line. Fill into foil sachets with a dual auger filler the re-blended granulation. Average Fill Weights: Target 0.500 g/sachet. The composition of Singulair™ Oral Granule 4 mg is shown below:

| Ingredient | mg/pouch | Source or vendor |
|---|---|---|
| Montelukast sodium | 4.16* | Merck & Co. |
| Mannitol (Pearlitol SD200) | 484.19 | Roquette Freres |
| Hydroxypropyl cellulose LF NF | 10.4 | Hercules Inc. |
| Purified water USP | (374)** | Merck & Co. |
| Magnesium stearate NF | 1.25 | Mallinckrodt |
| Total | 500.0 | |
| Pouch foil | | Algroup Lawson Mardon |

*equivalent to 4.0 mg montelukast free acid.
**removed during processing.

What is claimed is:

1. A flowable and dispersible pharmaceutical composition which comprises (i) granules comprising a pharmaceutically acceptable substrate which is spray-dried mannitol agglomerated with a pharmaceutically acceptable binder, and coated with montelukast sodium, and (ii) a pharmaceutically acceptable lubricant; wherein said binder is selected from hydroxypropyl cellulose, hydroxypropyl methylcellulose, methylcellulose, ethylcellulose and polyvinylpyrrolidone; and said granules are formed by coating said substrate with an aqueous solution consisting of montelukast sodium followed by drying.

2. A composition of claim 1 wherein said binder is hydroxypropyl cellulose.

3. A composition of claim 1 wherein said lubricant is magnesium stearate or talc.

4. A composition of claim 1 wherein said lubricant is magnesium stearate.

5. A flowable and dispersible pharmaceutical composition which comprises (i) granules comprising a pharmaceutically acceptable substrate which is spray-dried mannitol agglomerated with hydroxypropyl cellulose, said substrate being coated with montelukast sodium, and (ii) magnesium stearate, and said granules are formed by coating said substrate with an aqueous solution consisting of montelukast sodium followed by drying.

* * * * *